US009751906B2

(12) United States Patent
Minnaard et al.

(10) Patent No.: US 9,751,906 B2
(45) Date of Patent: Sep. 5, 2017

(54) SELECTIVE OXIDATION OF CARBOHYDRATES

(71) Applicant: Rijksuniversiteit Groningen, Groningen (NL)

(72) Inventors: Adriaan Jacobus Minnaard, Groningen (NL); Manuel Jäger, Groningen (NL); Aditya Lakshmi Narasimha Raju Gottumukkala, Groningen (NL); Johannes Gerardus de Vries, Groningen (NL); Andreas Alexander Bastian, Groningen (NL); Andreas Herrmann, Groningen (NL)

(73) Assignee: Rijksuniversiteit Groningen, Groningen (NL)

( * ) Notice: Subject to any disclaimer, the term of this patent is extended or adjusted under 35 U.S.C. 154(b) by 118 days.

(21) Appl. No.: 14/409,604

(22) PCT Filed: Jun. 20, 2013

(86) PCT No.: PCT/NL2013/050439
§ 371 (c)(1),
(2) Date: Dec. 19, 2014

(87) PCT Pub. No.: WO2013/191549
PCT Pub. Date: Dec. 27, 2013

(65) Prior Publication Data
US 2015/0218196 A1    Aug. 6, 2015

Related U.S. Application Data

(60) Provisional application No. 61/671,833, filed on Jul. 16, 2012.

(30) Foreign Application Priority Data

Jun. 20, 2012    (EP) .................................... 12172787

(51) Int. Cl.
C07H 15/222    (2006.01)
C07H 15/226    (2006.01)
C07H 15/224    (2006.01)
C07H 15/22    (2006.01)
C07H 15/232    (2006.01)
C07H 15/228    (2006.01)
C07H 15/234    (2006.01)
C07H 15/23    (2006.01)
C07H 1/00    (2006.01)
C07H 3/04    (2006.01)
C07H 3/06    (2006.01)
C07H 15/04    (2006.01)
C07H 15/18    (2006.01)
C07H 23/00    (2006.01)
C07H 3/02    (2006.01)
C07H 5/06    (2006.01)
C07H 17/04    (2006.01)

(52) U.S. Cl.
CPC ............. *C07H 15/222* (2013.01); *C07H 1/00* (2013.01); *C07H 3/02* (2013.01); *C07H 3/04* (2013.01); *C07H 3/06* (2013.01); *C07H 5/06* (2013.01); *C07H 15/04* (2013.01); *C07H 15/18* (2013.01); *C07H 15/22* (2013.01); *C07H 15/224* (2013.01); *C07H 15/226* (2013.01); *C07H 15/228* (2013.01); *C07H 15/23* (2013.01); *C07H 15/232* (2013.01); *C07H 15/234* (2013.01); *C07H 17/04* (2013.01); *C07H 23/00* (2013.01)

(58) Field of Classification Search
None
See application file for complete search history.

(56) References Cited

U.S. PATENT DOCUMENTS 4,683,298 A * 7/1987 Yalpani ................... C08B 15/06
536/18.7

FOREIGN PATENT DOCUMENTS

WO    WO-2013191549 A1    12/2013

OTHER PUBLICATIONS

Andrews, M. A., Voss, E. J., Gould, G. L., Klooster, W. T., & Koetzle, T. F. (1994). Regioselective Complexation of Unprotected Carbohydrates by Platinum (II): Synthesis, Structure, Complexation Equilibria, and Hydrogen-Bonding in Carbonate-Derived Bis (phosphine) platinum (II) Diolate and Alditolate Complexes. Journal of the American Chemical Soci.*
Volc, J., Sedmera, P., Halada, P., Daniel, G., Prikrylová, V., & Haltrich, D. (2002). C-3 oxidation of non-reducing sugars by a fungal pyranose dehydrogenase: spectral characterization. Journal of Molecular Catalysis B: Enzymatic, 17(2), 91-100.*
Zhang, W., & Robins, M. J. (1992). Removal of silyl protecting groups from hydroxyl functions with ammonium fluoride in methanol. Tetrahedron letters, 33(9), 1177-1180.*
"International Application Serial No. PCT/NL2013/050439, International Preliminary Report on Patentability mailed Aug. 29, 2014", (Aug. 29, 2014), 20 pgs.
"International Application Serial No. PCT/NL2013/050439, International Search Report mailed Aug. 19, 2013", (Aug. 19, 2013), 5 pgs.
"International Application Serial No. PCT/NL2013/050439, Written Opinion mailed Aug. 19, 2013", (Aug. 19, 2013), 9 pgs.
Gottumkkala, Aditya L, "Pd-Diimine: A Highly Selective Catalyst System for the Base-Free Oxidative Heck Reaction", The Journal of Organic Chemistry 76(9), (May 6, 2011), 3498-3501.

(Continued)

*Primary Examiner* — Shaojia Anna Jiang
*Assistant Examiner* — Dale R Miller
(74) *Attorney, Agent, or Firm* — Schwegman Lundberg & Woessner, P.A.

(57) ABSTRACT

The invention relates to the field of carbohydrate chemistry. Provided is a process for the regioselective oxidation of a single secondary hydroxy function of a carbohydrate substrate comprising two or more secondary hydroxy functions, comprising contacting the carbohydrate substrate in a solvent in the presence of a transition metal catalyst complex with an oxidizing agent to yield a mono-oxidized carbohydrate.

12 Claims, No Drawings

(56) References Cited

OTHER PUBLICATIONS

Hill, Nicholas J, et al., "Recent developments in the coordination chemistry of bis(imino)acenaphthene (BIAN) ligands with s- and p-block elements", Dalton Transactions: An international Journal of inorganic checmistry vol. 2, (Jan. 14, 2009), 213-384.

Maki-Arvela, Pavi, et al., "The effect of palladium dispersion and promoters on lactose oxidation kinetics", Research on Chemical Intermediates 36(4), (Jul. 1, 2010), 423-442.

Painter, Ron M, et al., "Selective Catalytic Oxidation of Glycerol to Dihydroxyacetone", Angewandte Chemie International Edition 49(49), (Oct. 28, 2010), 9456-9459.

Pearson, David M, et al., "Mechanistic Studies of the Oxidative Dehydrogenation of ethanol Using a Cationic Palladium Complex", Organometallics 28(13), (Jul. 13, 2009), 3896-3900.

Sen Gupta, Kalyan Kali, et al., "Kinetics and Mechanism of Oxidation of n-Glucopyranose 6-Phosphate and n-Ribofuranose 5-Phosphate by Chromium(VI) in Perchloric Acid Media", Carbohydrate Research vol. 139, (Jul. 15, 1985), 185-190.

Theander, Olof, et al., "The Oxidation of Glycosides V. Oxidation of Methyl 6-0-Trityl-B-D•glucopyranoside and Methyl 6-0-Trityl-{J-D-glucopyranoside with Chromium Trioxide", Acta Chemie Scandinavica (11), (Jan. 1, 1957), 1557-1564.

Tsuda, Yoshisuke, et al., "Regioselective Mono-oxidation of Non-protected Carbohydrates by Brominolysis of the Tin Intermediates 1", Chemical and Pharmaceutical Bulletin 37(9), (Jan. 1, 1989), 2344-2350.

Vuorinen, Tapani, et al., "C-Substituted pentos-2-uloses: synthesis and analysis by 1H- and 13C-n.m.r. spectroscopy", Carbohydrate Research 207(2), (Oct. 25, 1990), 185-210.

Painter, Ronald Michael, et al., "The Chemoselective Catalytic Oxidation of Alchohols, Diols, and Polyols to Ketones and Hydroxyketones", Stanford University, (2011), 110 pgs.

\* cited by examiner

SELECTIVE OXIDATION OF CARBOHYDRATES

PRIORITY APPLICATIONS

This application is a U.S. National Stage Filing under 35 U.S.C. 371 from International Application No. PCT/NL2013/050439, filed on 20 Jun. 2013, and published as WO 2013/191549 on 27 Dec. 2013, which application claims the benefit under 35 U.S.C. 119 to EP Application No. 12172787.9, filed on 20 Jun. 2012 and claims the benefit under 35 U.S.C. 119(e) to U.S. Provisional Application No. 61/671,833, filed on 16 Jul. 2012; which applications and publication are incorporated herein by reference in their entirety.

The invention relates to the field of carbohydrate chemistry. Carbohydrates, such as monosaccharides, disaccharides, oligosaccharides and polysaccharides, are important in the production of chemicals (as raw material), as building blocks for pharmaceuticals and as pharmaceuticals, food or fodder ingredients themselves. For example, the regioselective oxidation of an easily available carbohydrate as starting material may afford a polyhydroxy ketone which could be converted into a valuable product. Unfortunately, most carbohydrates are chemically difficult to handle. One of the most challenging aspects in the transformation of carbohydrates is to distinguish between the hydroxyl groups with equal or very similar reactivity. For example, the oxidation of a particular secondary hydroxyl group in saccharides leads mostly to mixtures of products as the oxidation method does not discriminate between the different hydroxyl groups.

Therefore, in chemical synthesis most often protecting group strategies are used wherein individual alcohol groups can be either exposed to or obscured from reactivity with oxidants through selective protection and deprotection.

For example, methyl allose is conventionally prepared from methyl glucose by protection of C(2)OH, C(4)OH and C(6)OH in two reaction steps, followed by reduction and deprotection (J. Carbohyd. Chem. 1994, 13, 4, 611-617). As another example, allose is currently prepared from glucose by protection (to di-acetone glucose), oxidation, reduction and deprotection in a process requiring 4 steps overall (Carbohyd. Res. 1972, 24, 192-197). The synthesis of protected 3-desoxy-3-amino glucose is currently carried out in 8 steps from methyl glucopyranoside (Carbohydrate Res. 1991, 210, 233-245).

Since the current protection-deprotection approach increases the total number of steps in the synthesis and decreases the overall yield, it is expensive, time and energy consuming and not atom-economical. Accordingly, the use of unprotected carbohydrates is highly preferred.

The selective oxidation of primary hydroxyl groups in unprotected carbohydrates is known in the art. Selective oxidizing agents that are able to directly distinguish secondary from primary alcohols have been shown to offer an attractive alternative to the use of protecting groups. For example, Liu et al (Chem. Pharm. Bull. 41(3) 491-501, 1993) reported a dibutyltin oxide-bromine method for the selective oxidation of a particular secondary hydroxyl group in glycosides, even if an unprotected primary hydroxyl group is present. See also the review by Arterburn (Tetrahedron 57 (2001) 9765-9788), and references cited therein. However, the selective catalytic oxidation of a single secondary hydroxyl group within an unprotected compound having multiple secondary hydroxyls is not known.

The present inventors therefore sought to provide a process allowing for regioselective oxidation of a secondary hydroxyl group in glycosides where two or more secondary hydroxyls are present. Preferably, they aimed towards a process having a high (>50%) yield, which allows for the use of unprotected carbohydrates, is economically attractive, and/or reduces the number of steps that are currently required for the synthesis of carbohydrate derivatives. More preferably, the method should be able to selectively oxidize one out of several secondary hydroxyl groups in an unprotected carbohydrate, e.g. a mono- or disaccharide, under mild conditions.

It was surprisingly found that at least some of these goals could be met by the use of a homogeneous transition metal complex catalyst. For example, using a palladium catalyst, the synthesis of methyl allose from methyl glucose was reduced from the conventional 5 steps to only 2 steps. As another example, synthesis of protected 3-desoxy-3-amino glucose from methyl glucopyranoside was reduced from 8 to 4 steps and the yield was considerably improved.

Accordingly, the invention relates to a process for the regioselective oxidation of a single secondary hydroxy function of a carbohydrate substrate comprising two or more secondary hydroxy functions, comprising contacting the carbohydrate substrate in a solvent in the presence of a transition metal catalyst complex with an oxidizing agent to yield a mono-oxidized carbohydrate and wherein the catalyst complex comprises at least one transition metal atom and one or more ligands comprising at least one nitrogen atom.

In chemistry, a regioselective reaction is one in which one direction of bond making or breaking occurs preferentially over all other possible directions. Reactions are termed completely (100%) regioselective if the discrimination is complete, or partially (x %), if the product of reaction at one site predominates over the product of reaction at other sites. The discrimination is sometimes also semi-quantitatively referred to in the art as high or low regioselectivity. Thus, as used herein, the term "regioselective oxidation" comprises both partial and complete regioselectivity. It pertains to an oxidation reaction which favors a single positional or structural isomer of the carbohydrate substrate, leading to its yield being greater than that of the other oxidation products in the reaction. According to the invention, the degree to which the oxidation is regioselective can vary. Typically, a method of the invention yields the major oxidation product in at least 2-fold, more preferably at least 2.5-fold, most preferably at least 3-fold excess of any other oxidation product(s).

As used herein, a transition metal is an element whose atom lies in groups 3 through 12 of the periodic table. In one embodiment, the transition metal catalyst complex for use in a method of the invention comprises palladium, rhodium, iridium, ruthenium, osmium, copper, manganese or iron. Preferably, the transition metal catalyst complex comprises palladium. For example, the catalyst complex comprises at least one transition metal atom, preferably a palladium atom, and one or more ligands comprising at least one nitrogen atom. In one aspect, the transition metal catalyst complex is a palladium phenanthroline complex in which the phenanthroline ligand is optionally substituted. For example, very good results were obtained with the catalyst [(2,9-dimethyl-1,10-phenanthroline)-Pd(μ-OAc)]$_2$(OTf)$_2$. In another embodiment, a catalyst complex is a palladium bis(aryl) acenapthenequinonediimine (BIAN) complex in which the BIAN ligand is optionally substituted. In addition to their convenient synthesis, BIAN ligands have important advantages, namely robust palladium complex formation, steric bulk discouraging dimerization, and resistance toward oxidation. BIAN ligands (see N. J. Hill et al., Dalton transactions (Cambridge, England: 2003) 2009, 9226, 240-253) have been used in the past for polymerisations (D. J. Tempel et al. J. Am. Chem. Soc. 2000, 122, 6686-6700), hydrogenations (A. M. Kluwer et al. (J. Am. Chem. Soc. 2005, 127, 15470-80) and for oxidative Heck reactions (Gottumukkala et al., The Journal of organic chemistry 2011, 76, 3498-501) Palladium catalysts have been widely investigated for alcohol oxidation and exhibit modest chemoselectivities and similar rates for the oxidation of primary and secondary alcohols. Painter et al. (Angew. Chem. Int. Ed. 2010, 49, 9456-9459) used a palladium phenanthroline catalyst for the chemoselective oxidation of the secondary alcohol in glycerol and 1,2-propanediol using benzoquinone or air as oxidant. Importantly, glycerol and 1,2-propanediol each contain only a single secondary hydroxyl group, and it is nowhere taught or suggested in the art that the catalyst is capable of selectively oxidizing one out of various secondary alcohols, as is shown in the present invention.

The skilled person will be able to determine the oxidation reaction conditions by routine optimization. The transition metal catalyst complex is preferably used in a molar ratio of 0.01-10 mol %, like 0.1-8 mol %, preferably 1-6 mol %, with respect to the carbohydrate substrate. Any suitable oxidizing agent can be used. In one embodiment, the oxidizing agent is oxygen, air, a quinone, a peroxide or a hydroperoxide. For example, the oxidizing agent is benzoquinone, 2,6-dichlorobenzoquinone or tert-butyl peroxybenzoate.

The performance of the reaction under aerobic conditions, e.g. under ambient air, oxygen atmosphere (1 atm) or a balloon of $O_2$. Air is preferred for economical reasons. Good results were obtained when the process is performed at a temperature between 0-100° C., e.g. 10-70° C., preferably at around room temperature. The total reaction time will depend on the specific circumstances. Exemplary incubation periods range from about 1-48 hr.

The oxidation reaction can be performed in any suitable solvent or solvent mixture. Stirring is recommended. It may be performed in water, an organic solvent or a mixture thereof. Suitable organic solvents include DMSO, dimethylformamide (DMF), tetrahydrofuran (THF), dioxane, acetonitril, hexamethylphosphoramide (HMPA), N-methyl-2-pyrrolidone (NMP) or any mixture thereof. In one embodiment, the solvent is DMSO. In another embodiment, it is a mixture of organic solvent and water, like acetonitrile/water in a ratio of 4:1 to 20:1 (v/v) or a mixture of dioxane/water in a ratio of 4:1 to 20:1 (v/v). In still another embodiment, the solvent is a mixture of dioxane/DMSO in a ratio of 4:1 to 20:1 (v/v). The carbohydrate substrate may be modified to improve its solubility in the solvent of the reaction. For example, a neamine-based antibiotic may be converted to its carbamate derivative in order to improve solubility in the reaction solvent.

As will be understood, a process according to the invention is advantageously applied for the oxidation of a carbohydrate substrate which only carries a minimal amount of protecting groups. In one embodiment, it does not carry any protecting groups on the two or more secondary hydroxyl groups. As used herein, the term "protecting group" refers to any moiety shielding the hydroxyl from chemical modification. For example, a hydroxyl group (—OH) can be converted into an acetyl group (—OOCCH$_3$) to protect it taking part in a certain step of the synthesis. In this case, the acetyl is the protecting group. Later it can easily be changed back into the original hydroxyl group.

The skilled person will understand that the invention can be practiced on any carbohydrate substrate of interest. As used herein, the term carbohydrate is a synonym of saccharide. Carbohydrates (saccharides) are divided into four chemical groupings: monosaccharides, disaccharides, oligosaccharides, and polysaccharides. In general, the monosaccharides and disaccharides, which are smaller (lower molecular weight) carbohydrates, are commonly referred to as sugars. Natural saccharides are generally built of simple carbohydrates called monosaccharides with general formula $(CH_2O)n$ where n is three or more. For example, the carbohydrate substrate is a monosaccharide, oligosaccharide (e.g. disaccharide, trisaccharide) or a polysaccharide. Exemplary substrates include starch, starch derivatives, cellulose, cellulose derivatives, chitin, inositol, and compounds derived from inositol. An example of an oligosaccharide is heparin.

In one embodiment, the carbohydrate substrate is it is a monosaccharide. A typical monosaccharide has the structure H—(CHOH)x(C═O)—(CHOH)y-H, that is, an aldehyde or ketone with many hydroxyl groups added, usually one on each carbon atom that is not part of the aldehyde or ketone functional group. Examples of monosaccharides are glucose, fructose, and glyceraldehydes. However, some biological substances commonly called "monosaccharides" do not conform to this formula (e.g., uronic acids and deoxy-sugars such as fucose), and there are many chemicals that do conform to this formula but are not considered to be monosaccharides (e.g., formaldehyde CH2O and inositol $(CH_2O)_6$). The open-chain form of a monosaccharide often coexists with a closed ring form where the aldehyde/ketone carbonyl group carbon (C═O) and hydroxyl group (—OH) react forming a hemiacetal with a new C—O—C bridge.

In a specific aspect, the invention provides a method for the manufacture of allose using methyl-α-D-glucopyranoside as carbohydrate substrate according to the following scheme.

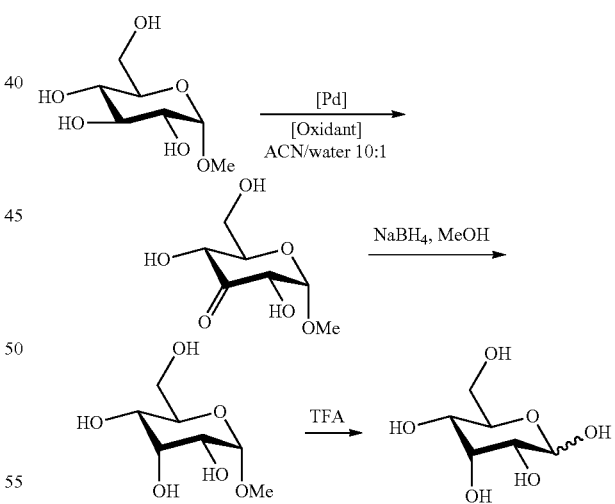

Allose is an aldohexose sugar and a C-3 epimer of glucose. It is a rare monosaccharide that occurs as a 6-O-cinnamyl glycoside in the leaves of the African shrub *Protea rubropilosa*. Extracts from the fresh-water alga *Ochromas malhamensis* contain this sugar but of unknown absolute configuration. It is soluble in water and practically insoluble in methanol.

Monosaccharides can be linked together into what are called oligosaccharides or polysaccharides in a large variety of ways. Generally speaking, the term oligosaccharide refers to any of a group of carbohydrates consisting of a small number (2 to 10) of simple sugar molecules.

For example, the carbohydrate is a disaccharide. Two joined monosaccharides are called a disaccharide and these are the simplest polysaccharides. Examples of disaccharides are maltose, lactose, trehalose, and sucrose. They are composed of two monosaccharide units bound together by a covalent bond known as a glycosidic linkage formed via a dehydration reaction, resulting in the loss of a hydrogen atom from one monosaccharide and a hydroxyl group from the other. The formula of unmodified disaccharides is $C_{12}H_{22}O_{11}$. Although there are numerous kinds of disaccharides, a handful of disaccharides are particularly notable. For example, disclosed herein below is the oxidation of methyl maltoside and methyl cellobioside.

Lactose, a disaccharide composed of one D-galactose molecule and one D-glucose molecule, occurs naturally in mammalian milk. The systematic name for lactose is O-β-D-galactopyranosyl-(1→4)-D-glucopyranose. Other notable disaccharides include maltose (two D-glucoses linked α-1, 4) and cellobiose (two D-glucoses linked β-1,4).

In yet another embodiment, the carbohydrate substrate is a polysaccharide. Polysaccharides are long carbohydrate molecules of repeated monomer units joined together by glycosidic bonds. They range in structure from linear to highly branched. Polysaccharides have a general formula of $Cx(H_2O)y$ where x is usually a large number between 200 and 2500. Considering that the repeating units in the polymer backbone are often six-carbon monosaccharides, the general formula can also be represented as $(C_6H_{10}O_5)n$ where $40 \leq n \leq 3000$. Polysaccharides are often quite heterogeneous, containing slight modifications of the repeating unit. Depending on the structure, these macromolecules can have distinct properties from their monosaccharide building blocks. They may be amorphous or even insoluble in water. When all the monosaccharides in a polysaccharide are the same type, the polysaccharide is called a homopolysaccharide or homoglycan, but when more than one type of monosaccharide is present they are called heteropolysaccharides or heteroglycans. Examples include storage polysaccharides such as starch and glycogen, and structural polysaccharides such as cellulose and chitin. Starch (a polymer of glucose) is used as a storage polysaccharide in plants, being found in the form of both amylose and the branched amylopectin. Polysaccharides also include callose or laminarin, chrysolaminarin, xylan, arabinoxylan, mannan, fucoidan and galactomannan.

In another aspect, the carbohydrate substrate is a glycoside. A glycoside is any molecule in which a carbohydrate is bonded through its anomeric carbon to another (non-carbohydrate) group via a glycosidic bond. Glycosides can be linked by an O-(an O-glycoside), N-(a glycosylamine), S-(a thioglycoside), C-(a C-glycoside) or Hal (halogen-glycoside) glycosidic bond. In a preferred embodiment, the invention provides a method for the regioselective oxidation of an O-glycoside, S-glycoside, N-glycoside, C-glycoside, or Halogen-glycoside. In one embodiment, the substrate is an O—$C_1$-$C_3$ alkyl glycoside, such as methyl glucoside (methyl α/β-glucopyranoside). It was surprisingly found that only the hydroxyl at the C3 position was oxidized to the corresponding 3-oxo-methyl glucoside.

In a specific aspect, the carbohydrate substrate is a neamine-based aminoglycoside, preferably selected from the group consisting of neomycin, apramycin, neamin, amikacin, paromomycin, ribostamycin, kanamycin, streptomycin framycetin, isepamicin or derivatives thereof. In one embodiment, a method of the invention allows for the selective oxidation of the hydroxyl group at the 3 position of ring I of the neamine-backbone. This opens up a wide variety of modification reactions to provide novel antibiotic analogs which are resistant to modification by bacterial enzymes, in particular the introduction of an inactivating negative charge by bacterial phosphotransferase (APH) which catalyzes ATP-dependent phosphorylation of a hydroxyl group. Hence, in one embodiment the invention provides a process for the regioselective oxidation of a single secondary hydroxy of a neamine-based aminoglycoside, comprising contacting the aminoglycoside substrate in a solvent in the presence of a transition metal catalyst complex with an oxidizing agent to yield a mono-oxidized neamine-based aminoglycoside.

In one embodiment of the process according to the invention, the mono-oxidized carbohydrate is subjected to a further derivatization reaction. Further derivatizations may be performed at the ketone and/or any other position of interest. Further derivatization may be performed chemically or enzymatically. For example, derivatization may comprise reduction, reductive amination, acetalisation, diazotation, hydrocyanation, imination, oximation, hydrazination, de-oxygenation, alkylation and any combination thereof. Procedures which minimize or avoid any prior protection or deprotection steps are of course preferred.

In one aspect, further derivatization comprises reduction, e.g. the reduction of the keto-glucose to give allose. In another aspect, derivatization comprises reductive amination, like the reductive amination of the keto N-acetylamino glucose to the di-amino glucose. In a further embodiment, the mono-oxidized carbohydrate is an oxidized neamine-based aminoglycoside antibiotic. The oxidation (and if needed further derivatisation of the ketone) renders the antibiotic resistant to inactivation by bacterial phosphorylation. The oxidized antibiotic may be further derivatized at the ketone and/or any other position of interest, such as the N-1 or the N-3 position of the 2-desoxy-streptamine ring which renders the antibiotic resistant to inactivation by bacterial acylation.

The present application finds many interesting commercial applications. For example, it can be used for the selective synthesis of natural or rare (unnatural) carbohydrates from more readily available carbohydrates, for the preparation of non-natural carbohydrates and related compounds such as amino-sugars, desoxy sugars, fluorosugars or for the selective modification of glycolipids, glycopolyketides, glycoproteins with the aim to change their behaviour. It also offers the ability to conjugate carbohydrates to other molecules in order to probe the function of the carbohydrate. For example, by coupling the carbohydrate at the ketofunction, for example via reductive amination, to a fluorophore, a chemical probe or a chemical tag, for example biotin, the function and/or localisation (e.g. in a cell) of the parent carbohydrate can be determined.

Also provided are compounds obtainable by a method of the invention. In one embodiment, it is a di- or polysaccharide in which only a single secondary hydroxyl group has been oxidized to a ketone. For example, it is a carbohydrate comprising one or more secondary hydroxyls and a single ketone. In one embodiment, it is a O-glycoside, a glycosylamine, a thioglycoside, a C-glycoside or halogenglycoside comprising one or more secondary hydroxyls and a single ketone. In a specific aspect, the invention provides a compound selected from the group consisting of methyl-2-deoxy-β-D-erythro-hexopyranoside-3-ulose, methyl-β-3-ketomaltoside, methyl-β-3-ketocellobioside, (6-O-benzoyl)-methyl-α-D-ribo-hexapyranoside-3-ulose, (6-O-tert-butyldiphenylsilyl)-methyl-α-D-ribo-hexapyranoside-3-ulose, methyl-3-acetamido-α-D-ribo-hexapyranoside, 3'-keto-neomycin B, thiophenyl-β-D-ribo-hexopyranoside-3-ulose and phenyl-α-D-ribo-hexapyranoside-3-ulose.

These compounds have not been disclosed in the art and find their use e.g. in the synthesis of pharmaceutical products or compounds for medical diagnostics.

EXPERIMENTAL SECTION

Example 1

Synthesis of Oxo-glucopyranosides

General Procedure a (Acetonitrile/Water as Solvent)

Methyl glycoside (4 mmol, 1.0 eq) and 2,6-dichlorobenzoquinone (12 mmol, 3.0 eq) were suspended in acetonitrile/de-ionized water (10:1, 0.3 M). The catalyst [(2,9-dimethyl-1,10-phenanthroline)-Pd(μ-OAc)]$_2$(OTf)$_2$ (0.1 mmol, 2.5 mol %) was added and the mixture was stirred at rt until the reaction was finished, as indicated by TLC (DCM/MeOH 5:1). Toluene (50 mL) was added and the mixture was extracted twice with water (7 mL). The combined water layers were washed once with ethyl ether (35 mL), filtered and concentrated in vacuo to give the pure keto-sugar.

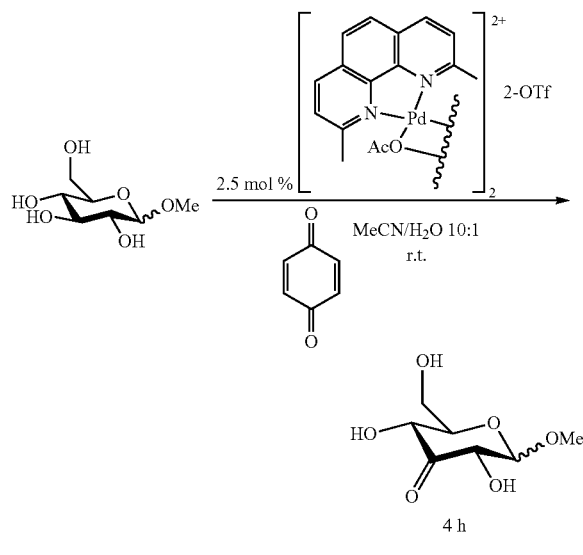

General Procedure B (DMSO as Solvent)

Methyl glycoside (0.84 mmol, 1.0 eq) and 2,6-dichlorobenzoquinone (2.5 mmol, 3.0 eq) were dissolved in DMSO (0.3-0.9 M). The catalyst [(2,9-dimethyl-1,10-phenanthroline)-Pd(μ-OAc)]$_2$(OTf)$_2$ (0.021 mmol, 2.5 mol %) was added and the mixture was stirred at rt until the reaction was finished, as indicated by NMR-spectroscopy. 10 mL water was added, the mixture was filtered and the precipitates were washed with water (3×2 mL). The water layer was passed over a charcoal column (10 g of charcoal). The charcoal column was washed with 4 column volumes of water and subsequently the product was eluted with water/acetonitrile 3:1 (3 column volumes). The crude product was purified by silica column chromatography (automated, the crude product was coated on charcoal, eluent: DCM/acetone/MeOH/water mixtures).

General Procedure C (Dioxane/Water as Solvent and 2,6-dichlorobenzoquinone as Oxidant)

Methyl glycoside (0.15 mmol, 1.0 eq) and 2,6-dichlorobenzoquinone (0.45 mmol, 3.0 eq) were suspended in dioxane/de-ionized water (5:1, 0.3 M). The catalyst [(2,9-dimethyl-1,10-phenanthroline)-Pd(μ-OAc)]$_2$(OTf)$_2$ (0.1 mmol, 2.5 mol %) was added and the mixture was stirred at rt until the reaction was finished, as indicated by TLC (DCM/MeOH 5:1). Toluene (2 mL) was added and the mixture was extracted twice with water (0.26 mL). The combined water layers were washed once with ethyl ether (1.3 mL), filtered and concentrated in vacuo to give the pure keto-sugar.

General Procedure D (Dioxane/DMSO as Solvent and 2,6-dichlorobenzoquinone as Oxidant)

Methyl glycoside (0.15 mmol, 1.0 eq) and 2,6-dichlorobenzoquinone (0.45 mmol, 3.0 eq) were suspended in dioxane/DMSO (10:1 or 20:1, 0.3 M). The catalyst [(2,9-dimethyl-1,10-phenanthroline)-Pd(μ-OAc)]$_2$(OTf)$_2$ (0.1 mmol, 2.5 mol %) was added and the mixture was stirred at rt until the reaction was finished, as indicated by TLC (DCM/MeOH 5:1). Toluene (2 mL) was added and the mixture was extracted twice with water (0.26 mL). The combined water layers were washed once with ethyl ether (1.3 mL), filtered and concentrated in vacuo to give the pure keto-sugar (contains still DMSO.

General Procedure E (Dioxane/Water as Solvent and Benzoquinone as Oxidant)

Methyl glycoside (0.25 mmol, 1.0 eq) and benzoquinone (0.75 mmol, 3.0 eq) were suspended in dioxane/de-ionized water (5:1, 0.3 M). The catalyst [(2,9-dimethyl-1,10-phenanthroline)-Pd(μ-OAc)]$_2$(OTf)$_2$ (1.25 μmol, 0.5 mol %) was added and the mixture was stirred at rt until the reaction was finished, as indicated by TLC (DCM/MeOH 5:1). Toluene (2 mL) was added and the mixture was extracted twice with water (0.26 mL). The combined water layers were washed once with ethyl ether (1.3 mL), filtered and concentrated in vacuo to give the pure keto-sugar.

General Procedure F (Dioxane/DMSO as Solvent and Benzoquinone as Oxidant)

Methyl glycoside (0.25 mmol, 1.0 eq) and 2,6-dichlorobenzoquinone (0.75 mmol, 3.0 eq) were suspended in dioxane/DMSO (10:1 or 20:1, 0.3 M). The catalyst [(2,9-dimethyl-1,10-phenanthroline)-Pd(μ-OAc)]$_2$(OTf)$_2$ (1.25 μmol, 0.5 mol %) was added and the mixture was stirred at rt until the reaction was finished, as indicated by TLC (DCM/MeOH 5:1). Toluene (2 mL) was added and the mixture was extracted twice with water (0.26 mL). The combined water layers were washed once with ethyl ether (1.3 mL), filtered and concentrated in vacuo to give the pure keto-sugar (contains still DMSO.

Example 2

Synthesis of Methyl-α-D-ribo-hexapyranoside-3-ulose

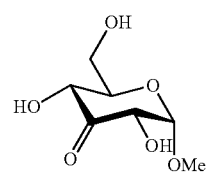

Methyl-α-glucopyranoside (777 mg, 4.0 mmol, 1.0 eq) was oxidized according to general procedure A using 2,6- dichloro-1,4-benzoquinone (2.12 g, 12.0 mmol, 3.0 eq.) and [(2,9-dimethyl-1,10-phenanthroline)-Pd(μ-OAc)]$_2$(OTf)$_2$ (105 mg, 2.5 mol %) in acetonitrile/water (13.4 mL, 10:1, 0.3 M in substrate) within 3 h. Methyl-α-D-ribo-hexapyranosid-3-ulose (751 mg, 3.9 mmol) was isolated in 98% yield as a dark brown solid. $^1$H NMR[1] (400 MHz, 298 K, DMSO-d$_6$): δ=4.95 (d, J=4.2 Hz, 1H), 4.29 (dd, J=4.2, 1.5 Hz, 1H), 4.07 (dd, J=9.8, 1.4 Hz, 1H), 3.69 (dd, J=11.9, 1.9 Hz, 1H), 3.59 (dd, J=11.9, 4.9 Hz, 1H), 3.46 (ddd, J=9.7, 4.9, 1.8 Hz, 1H), 3.26 (s, 3H). $^{13}$C NMR (50 MHz, DMSO-d$_6$): δ=206.1, 102.2, 75.4, 74.6, 71.9, 60.7, 54.4. HRMS (ESI) calculated for C$_7$H$_{12}$O$_6$Na ([M+Na]$^+$): 215.0526. found: 215.0523 IR ν$_{max}$/cm$^{-1}$: 3436 (OH), 2947 (C—H), 1736 (C=O), 1031 (C—O).

Example 3

Synthesis of Methyl-β-D-ribo-hexapyranoside-3-ulose

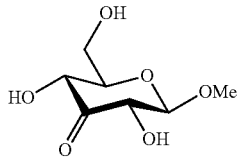

Methyl-β-glucopyranoside (777 mg, 4.0 mmol, 1.0 eq.) was oxidized according to general procedure A using 2,6-dichloro-1,4-benzoquinone (2.12 g, 12.0 mmol, 3.0 eq) and [(2,9-dimethyl-1,10-phenanthroline)-Pd(μ-OAc)]$_2$(OTf)$_2$ (105 mg, 2.5 mol %) in acetonitrile/water (13.4 mL, 10:1, 0.3 M in substrate) within 5 h. Methyl-β-D-ribo-hexapyranosid-3-ulose (686 mg, 3.6 mmol) was isolated in 89% yield as a dark brown solid. $^1$H NMR[2][3] (400 MHz, 298 K, DMSO-d$_6$): δ=4.20 (d, J=8.0 Hz, 1H), 4.05 (dd, J=10.2, 1.6 Hz, 1H), 3.97 (dd, J=8.0, 1.6 Hz, 1H), 3.73 (dd, J=11.9, 1.7 Hz, 1H), 3.58 (dd, J=12.0, 5.1 Hz, 1H), 3.45 (s, 3H), 3.21 (ddd, J=10.2, 5.1, 1.7 Hz, 1H). $^{13}$C NMR (50 MHz, 298 K, DMSO-d$_6$): δ=206.3, 104.8, 76.6, 76.6, 72.2, 60.8, 56.2. HRMS (ESI) calculated for C$_7$H$_{12}$O$_6$Na ([M+Na]$^+$): 215.0526. found: 215.0523 IR ν$_{max}$/cm$^{-1}$: 3382 (OH), 2953 (C—H), 1738 (C=O), 1036 (C—O).

Example 4

Synthesis of Methyl-2-(acetylamino)-2-deoxy-α-D-ribo-hexapyranosid-3-ulose

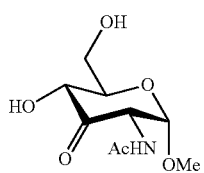

Methyl-N-acetyl-glucosamine-pyranoside (941 mg, 4 mmol, 1.0 eq) was oxidized according to general procedure A using 2,6-dichloro-1,4-benzoquinone (2.12 g, 12.0 mmol, 3.0 eq) and [(2,9-dimethyl-1,10-phenanthroline)-Pd(μ-OAc)]$_2$(OTf)$_2$ (105 mg, 2.5 mol %) in acetonitrile/water (13.4 mL, 10:1, 0.3 M in substrate) within 4 h. Methyl-2-(acetylamino)-2-deoxy-α-D-ribo-hexapyranosid-3-ulose (792 mg, 3.4 mmol) was isolated in 85% as a dark brown solid. $^1$H NMR[4] (400 MHz, 298 K, DMSO-d$_6$): δ=8.02 (d, J=8.2 Hz, 1H), 5.49 (d, J=6.0 Hz, 1H), 4.98 (d, J=4.0 Hz, 1H), 4.84 (s, 1H), 4.77 (dd, J=7.9, 3.7 Hz, 1H), 4.17 (dd, J=9.5, 5.5 Hz, 1H), 3.71 (d, J=11.7 Hz, 1H), 3.66-3.57 (m, 1H), 3.57-3.49 (m, 1H), 3.26 (s, 3H), 1.91 (s, 3H). $^{13}$C NMR (50 MHz, DMSO-d$_6$): δ=203.0, 169.7, 100.6, 75.6, 72.2, 60.7, 58.6, 54.5, 22.2. HRMS (ESI) calculated for C$_9$H$_{15}$NO$_6$H ([M+H]$^+$): 234.0972. found: 234.0972, C$_9$H$_{15}$O$_6$Na ([M+Na]$^+$): 256.0792. found: 256.0790 IR ν$_{max}$/cm$^{-1}$: 3296 (OH), 2878 (C—H), 1734 (C=O), 1035 (C—O).

Example 5

Synthesis of (6-O-tert-butyl-diphenylsilyl)-methyl-α-D-ribo-hexapyranoside-3-ulose (OxTBDPS-MGlc)

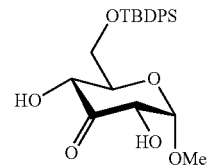

Methyl-C6-TBDPS-α-glucopyranoside (364 mg, 0.84 mmol, 1.0 eq) and 2,6-dichloro-1,4-benzoquinone (447 mg, 2.53 mmol, 3.0 eq) were dissolved in DMSO (0.93 mL, 0.9 M) and [(2,9-dimethyl-1,10-phenanthroline)-Pd(μ-OAc)]$_2$(OTf)$_2$ (22 mg, 2.5 mol %) was added. The mixture was stirred at rt for 30 min. The reaction was quenched by adding water (12 mL) and the resulting precipitate was decanted. The precipitate was dissolved in MeOH/Et$_2$O to transfer it. Concentration of the dissolved precipitate in vacuo gave 774 mg of crude product, which was purified by silica column chromatography (eluent: gradient of acetone/MeOH 1:1 in DCM 0%-3%). 239 mg of pure (6-O-tert-butyl-diphenylsilyl)-methyl-α-D-ribo-hexapyranoside-3-ulose (0.56 mmol, 66%) was isolated as a white foam. $^1$H NMR (400 MHz, CD$_3$OD): δ 7.82-7.64 (m, 4H), 7.54-7.28 (m, 6H), 5.08 (d, J=4.3 Hz, 1H), 4.40 (dd, J=4.3, 1.4 Hz, 1H), 4.34 (d, J=9.8, 1.4 Hz, 1H), 4.00 (d, J=3.3 Hz, 2H), 3.74 (dt, J=9.7, 3.3 Hz, 1H), 3.40 (s, 3H), 1.07 (s, 9H). $^{13}$C NMR (101 MHz, CD$_3$OD): δ=207.2, 136.9, 136.9, 134.8, 134.7, 131.0, 131.0, 128.9, 103.8, 77.0, 76.3, 73.6, 64.8, 55.8, 27.4, 20.3. HRMS (ESI) calculated for C$_{23}$H$_{30}$O$_6$SiNa ([M+Na]$^+$): 453.1704. found: 453.1643.

Example 6

Synthesis of (6-O-benzoyl)-methyl-α-D-ribo-hexapyranoside-3-ulose (OxBzMGlc)

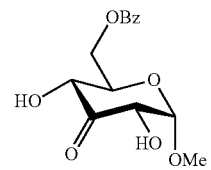

(6-O-benzoyl)-methyl-α-D-glucopyranoside (251 mg, 0.84 mmol, 1.0 eq) and 2,6-dichloro-1,4-benzoquinone (447 mg, 2.53 mmol, 3.0 eq) were dissolved in DMSO (0.93 mL, 0.9 M) and [(2,9-dimethyl-1,10-phenanthroline)-Pd(μ-OAc)]$_2$(OTf)$_2$ (22 mg, 2.5 mol %) was added. The mixture was stirred at rt for 1 h. The reaction was quenched by adding water (10 mL), the resulting precipitate was filtered and the filter was washed with water (1×10 mL, 1×5 mL). The water layer was passed over a charcoal column (10 g charcoal). The charcoal column was washed with 4.5 column volumes of water, 3 column volumes of water/acetonitrile (3:1) and subsequently the product was eluted with 3 column volumes of DCM/acetone/MeOH/water (56/20/20/4) which gave 409 mg of crude product. The crude product was purified by silica column chromatography (automated, eluent: gradient of DCM/MeOH 0-10%). 113 mg of pure (6-O-benzoyl)-methyl-α-D-ribo-hexapyranoside-3-ulose (45%) was isolated as a white foam.

$^1$H NMR (400 MHz, CD$_3$OD): δ=8.09-8.03 (m, 2H), 7.65-7.58 (m, 1H), 7.52-7.46 (m, 2H), 5.08 (d, J=4.3 Hz, 1H), 4.72 (dd, J=11.9, 2.2 Hz, 1H), 4.57 (dd, J=11.9, 5.7 Hz, 1H), 4.48 (dd, J=4.3, 1.5 Hz, 1H), 4.34 (dd, J=10.0, 1.4 Hz, 1H), 3.99 (ddd, J=9.9, 5.6, 2.1 Hz, 1H), 3.42 (s, 3H). $^{13}$C NMR (101 MHz, CD$_3$OD): δ=206.3, 167.8, 134.6, 131.3, 130.7, 129.8, 103.8, 76.2, 74.2, 74.0, 65.3, 55.9. HRMS (ESI) calculated for C$_{14}$H$_{16}$O$_7$Na ([M+Na]$^+$): 319.0788. found: 319.0739.

Example 7

Synthesis of Methyl-β-3-ketomaltoside

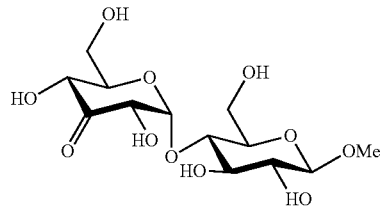

Methyl-β-maltoside (300 mg, 0.84 mmol, 1.0 eq) was oxidized according to general procedure B using 2,6-dichloro-1,4-benzoquinone (447 mg, 2.53 mmol, 3.0 eq) and [(2,9-dimethyl-1,10-phenanthroline)-Pd(μ-OAc)]$_2$(OTf)$_2$ (22 mg, 2.5 mol %) in DMSO (0.94 mL, 0.9 M) within 3.5 h (reaction stopped at 87% conversion). 10 mL water was added, the mixture was filtered and the precipitates were washed with water (4×2 mL). The water layer was passed over a charcoal column (10 g of charcoal). The charcoal column was washed with 4 column volumes of water and subsequently the product was eluted with water/acetonitrile 3:1 (2 column volumes). 308 mg of product, ~70% pure according to NMR, was isolated after concentration in vacuo. 125 mg of pure methyl-β-ketomaltoside (0.25 mmol, 42%) was isolated after column chromatography (eluent: DCM/acetone/MeOH/water 56:20:20:4) along with 20 mg of mixed fractions. $^1$H NMR (400 MHz, CD$_3$OD): δ=5.62 (d, J=4.5 Hz, 1H), 4.45 (dd, J=4.5, 1.6 Hz, 1H), 4.25 (dd, J=9.6, 1.5 Hz, 1H), 4.15 (d, J=7.8 Hz, 1H), 3.92-3.70 (m, 5H), 3.60-3.55 (m, 2H), 3.51 (s, 3H), 3.34-3.31 (m, 1H), 3.21-3.15 (m, 1H). $^{13}$C NMR (101 MHz, CD$_3$OD): δ=207.2, 105.4, 104.8, 80.6, 78.0, 77.7, 76.6, 76.4, 74.8, 73.4, 62.6, 62.1, 57.5. HRMS (ESI) calculated for C$_{13}$H$_{22}$O$_{11}$Na ([M+Na]$^+$): 377.1054. found: 377.1048.

Example 8

Synthesis of Methyl-β-3-ketocellobioside

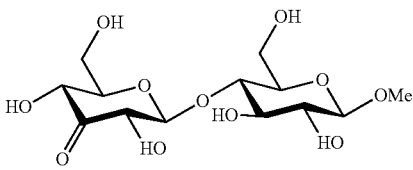

Methyl-β-cellobioside (300 mg, 0.84 mmol, 1.0 eq) was oxidized according to general procedure B using 2,6-dichloro-1,4-benzoquinone (447 mg, 2.53 mmol, 3.0 eq) and [(2,9-dimethyl-1,10-phenanthroline)-Pd(μ-OAc)]$_2$(OTf)$_2$ (22 mg, 2.5 mol %) in DMSO (0.94 mL, 0.9 M) within 2 h. 88 mg of pure methyl-β-3-ketocellobioside (0.25 mmol, 30%) was isolated after column chromatography (eluent: DCM/acetone/MeOH/water 56:20:20:4) along with 38 mg (13%) of starting material. $^1$H NMR (400 MHz, CD$_3$OD): δ=4.55 (d, J=7.9 Hz, 1H), 4.25 (dd, J=10.2, 1.5 Hz, 1H), 4.22 (d, J=7.8 Hz, 1H), 4.19 (dd, J=8.0, 1.6 Hz, 1H), 3.95 (dd, J=12.1, 2.0 Hz, 1H), 3.88 (qd, J=12.2, 3.1 Hz, 3H), 3.78 (dd, J=12.1, 5.0 Hz, 1H), 3.66 (t, J=9.2 Hz, 1H), 3.56 (t, J=9.0 Hz, 1H), 3.53 (s, 3H), 3.44-3.34 (m, 2H), 3.24 (dd, J=9.0, 8.0 Hz, 1H). $^{13}$C NMR (101 MHz, CD$_3$OD): δ=206.8, 105.9, 105.4, 80.5, 78.4, 78.4, 76.6, 76.53, 75.0, 73.6, 62.5, 61.6, 57.5.

HRMS (ESI) calculated for C$_{13}$H$_{22}$O$_{11}$Na ([M+Na]$^+$): 377.1054. found: 377.1002.

Example 9

Comparison Between Various Oxidizing Agents

Oxygen (MeCN/Water as Solvent)
Methyl-α-glucopyranoside (100 mg, 0.52 mmol, 1.0 eq) was suspended in acetonitrile/de-ionized water (10:1, 0.3 M). The catalyst [(2,9-dimethyl-1,10-phenanthroline)-Pd(μ-OAc)]$_2$(OTf)$_2$ (13 mg, 13 μmol, 2.5 mol %) was added and the mixture was stirred at room temperature (rt) under oxygen atmosphere (1 atm). The reaction stopped after 43 h at 45% conversion as indicated by $^1$H-NMR.

Oxygen (DMSO as Solvent)
Methyl-α-glucopyranoside (100 mg, 0.52 mmol, 1.0 eq) was dissolved in DMSO (0.57 mL, 0.3 M). The catalyst [(2,9-dimethyl-1,10-phenanthroline)-Pd(μ-OAc)]$_2$(OTf)$_2$ (13 mg, 13 μmol, 2.5 mol %) was added and the mixture was stirred at rt under oxygen atmosphere (1 atm). The reaction stopped after 43 h at 69% conversion as indicated by $^1$H-NMR.

Tert-butyl peroxybenzoate (DMSO as Solvent)
Methyl-α-glucopyranoside (30 mg, 0.15 mmol, 1.0 eq) and tert-butyl peroxybenzoate (74 μL, 0.46 mmol, 3.0 eq) were dissolved in DMSO (0.17 mL, 0.9 M). The catalyst [(2,9-dimethyl-1,10-phenanthroline)-Pd(μ-OAc)]$_2$(OTf)$_2$ (4 mg, 3.8 μmol, 2.5 mol %) was added and the mixture was stirred at rt. The reaction stopped after 13 days at 67% conversion as indicated by $^1$H-NMR.

Air (Oxygen) as Oxidant (DMSO as Solvent)
Methyl-α-glucopyranoside (30 mg, 0.15 mmol, 1.0 eq) was dissolved in DMSO (0.5 mL, 0.3 M). The catalyst [(2,9-dimethyl-1,10-phenanthroline)-Pd(μ-OAc)]$_2$(OTf)$_2$ (4 mg, 3.8 μmol, 2.5 mol %) was added. The mixture was stirred at rt with a gentle stream of air. The reaction stopped after 13 days at 73% conversion as indicated by ¹H-NMR.

Cumene Hydroperoxide as Oxidants (DMSO as Solvent)

Methyl-α-glucopyranoside (30 mg, 0.15 mmol, 1.0 eq) and cumene hydroperoxide (86 μL, 0.46 mmol, 3.0 eq) were dissolved in DMSO (0.5 mL, 0.3 M). The catalyst [(2,9-dimethyl-1,10-phenanthroline)-Pd(μ-OAc)]$_2$(OTf)$_2$ (4 mg, 3.8 μmol, 2.5 mol %) was added and the mixture was stirred at rt. The reaction stopped after 13 days at 69% conversion as indicated by ¹H-NMR.

Hydrogen Peroxide as Oxidants (DMSO as Solvent)

Methyl-α-glucopyranoside (30 mg, 0.15 mmol, 1.0 eq) and hydrogen peroxide 30% (46 μL, 0.46 mmol, 3.0 eq) were dissolved in DMSO (0.5 mL, 0.3 M). The catalyst [(2,9-dimethyl-1,10-phenanthroline)-Pd(μ-OAc)]$_2$(OTf)$_2$ (4 mg, 3.8 μmol, 2.5 mol %) was added and the mixture was stirred at rt. The reaction showed 49% conversion after 16 days as indicated by ¹H-NMR.

Example 10

Reduction of the Mono-Oxidized Carbohydrates

Methyl-α-allopyranoside

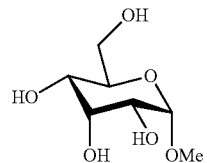

was dissolved in MeOH (8.5 mL) and the mixture was cooled to 0° C. Sodium borohydride (118 mg, 3.12 mmol, 3.0 eq) was added and the mixture stirred for 30 min at rt. Excess borohydride was destroyed by addition of acidic ion exchange resin (Amberlite® 120 H⁺-form), the mixture was filtered over celite and concentrated in vacuo. The residue was co-evaporated with MeOH (3×10 mL) to give 193 mg (0.99 mmol, 95%) of methyl-α-allopyranoside as reddish sticky oil.

¹H NMR[3] (400 MHz, CD$_3$OD): δ=4.69 (d, J=3.8 Hz, 1H), 3.98 (appears as t, J=3.2 Hz, 1H), 3.88-3.82 (m, 1H), 3.74-3.67 (m, 2H), 3.60 (appears as t, J=3.6 Hz, 1H), 3.47 (dd, J=9.7, 3.1 Hz, 1H), 3.43 (s, 3H). ¹³C NMR (101 MHz, CD$_3$OD) δ=101.6, 73.6, 69.6, 69.1, 68.4, 62.8, 56.2. HRMS (ESI) calculated for C$_7$H$_{14}$O$_6$Na ([M+Na]⁺): 217.0683. found: 217.0682.

Example 11

Oximation of the Mono-Oxidized Carbohydrate

A. E/Z-Methyl-3-O-methyloxime-α-D-ribo-hexapyranoside

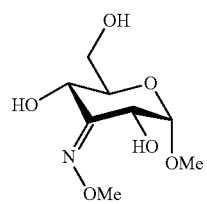

Methyl-α-D-ribo-hexapyranosid-3-ulose (330 mg, 1.70 mmol, 1.0 eq), O-methylhydroxylamine hydrochloride (215 mg, 2.58 mmol, 1.5 eq) and NaHCO$_3$ (218 mg, 2.58 mmol, 1.5 eq) were heated at reflux for 2 h in methanol (13 mL). After filtration to remove salts, and evaporation of the solvent, the residue was extracted with hot ethyl acetate. The extract was passed over a short silica gel column and was concentrated in vacuo, to give methyl-3-O-methyloxime-α-D-ribo-hexapyranoside (344 mg, 1.55 mmol, 92% as a mixture of E/Z isomers) as a sticky yellow solid. HRMS (ESI) exact mass calculated for C$_8$H$_{15}$NO$_6$H ([M+H]⁺): 222.0972. found: 222.0970, C$_9$H$_{15}$O$_6$Na ([M+Na]⁺): 244.0792. found: 244.0789 IR $v_{max}$/cm⁻¹: 3454 (OH), 2946 (C—H), 1034 (C—O).

B. E/Z-Methyl-3-O-methyloxime-β-D-ribo-hexapyranoside

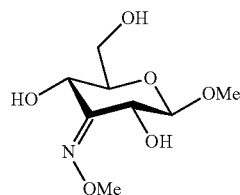

Methyl-β-D-ribo-hexapyranosid-3-ulose (300 mg, 1.56 mmol, 1.0 eq), O-methylhydroxylamine hydrochloride (195 mg, 2.34 mmol, 1.5 eq) and NaHCO$_3$ (197 mg, 2.34 mmol, 1.5 eq) in methanol (13 mL) were heated at reflux for 2.5 h. After filtration to remove salts and evaporation of the solvent, the residue was extracted with hot ethyl acetate and the extract was passed over a short silica gel column. Removing the solvent in vacuo gave methyl-3-O-methyloxime-β-D-ribo-hexapyranoside (311 mg, 1.41 mmol, 90% as a mixture of E/Z isomers) as a sticky yellow solid. HRMS (ESI) exact mass calculated for C$_8$H$_{15}$NO$_6$H ([M+H]⁺): 222.0972. found: 222.0970, C$_9$H$_{15}$O$_6$Na ([M+Na]⁺): 244.0792. found: 244.0789 IR $v_{max}$/cm⁻¹: 3447 (OH), 2946 (C—H), 1031 (C—O).

C. E/Z-Methyl-2-(acetamido)-2-desoxy-3-O-methyloxime-α-D-ribo-hexapyranoside

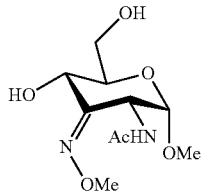

2-(acetamino)-2-desoxy-α-D-ribo-hexapyranosid-3-ulose (300 mg, 1.37 mmol, 1.0 eq), O-methylhydroxylamine hydrochloride (171 mg, 2.05 mmol, 1.5 eq) and NaHCO$_3$ (172 mg, 2.05 mmol, 1.5 eq) in methanol (12 mL) were heated under reflux for 3 h. After filtration to remove salts and evaporation of the solvent, the residue was extracted with hot ethyl acetate and the extract was passed over a short silica gel column and was concentrated in vacuo, to give methyl-2-(acetamido)-2-desoxy-3-O-methyloxime-α-D-ribo-hexapyranoside (308 mg, 1.17 mmol, 86% as a mixture of E/Z isomers) as a sticky yellow solid. HRMS (ESI) exact mass calculated for C$_{10}$H$_{18}$N$_2$O$_6$H ([M+H]⁺): 263.1238.

found: 263.1235, $C_{10}H_{18}N_2O_6Na$ ([M+Na]$^+$): 285.1057. found: 285.1054 IR $v_{max}$/cm$^{-1}$: 3447 (OH), 2946 (C—H), 1654 (OCN), 1031 (C—O).

Example 12

Synthesis of Methyl-3-amino-α-D-ribo-hexapyranoside

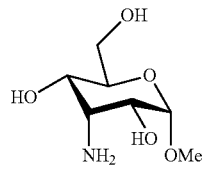

E/Z-Methyl-3-O-methyloxime-α-D-ribo-hexapyranoside (Example 11A; 240 mg, 1.08 mmol, 1.0 eq) in acetic acid (5 mL) was hydrogenated over platinum(IV) oxide (25 mg, 0.11 mmol, 10 mol %) under hydrogen pressure (5 bar) for 24 h. The mixture was passed over a short celite column and concentrated in vacuo, to give methyl-3-amino-α-D-ribo-hexapyranoside (208 mg, 1.08 mmol, 99%) as a sticky slightly yellow solid. The product was directly used in a subsequent per-acetylation reaction. $^1$H NMR (400 MHz, 298 K, DMSO-d$_6$): δ=5.21 (d, J=3.1 Hz, 1H), 4.31-4.26 (m, 2H), 4.23 (dd, J=9.9, 4.1 Hz, 1H), 4.15 (dd, J=11.0, 4.9 Hz, 2H), 4.00 (d, J=4.2 Hz, 1H), 3.90 (s, 3H).

Example 13

Synthesis of Methyl-3-acetamido-2,4,6-tri-O-acetyl-3-deoxy-α-D-ribo-hexapyranoside

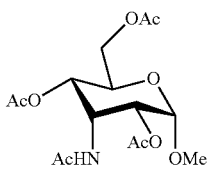

Methyl-3-amino-α-D-ribo-hexapyranosid (Example 12; 208 mg, 1.08 mmol, 1.0 eq) was dissolved in dry pyridine (2.4 mL) and acetic anhydride (1 mL, 9.9 mmol, 8 eq). The reaction mixture was stirred overnight. The mixture was co-evaporated with toluene (1 mL) and purified by automated silicagel column chromatography (GRACE) with a solvent gradient of pentane/EtOAc (1:1 to pure EtOAc) to give methyl-3-acetamido-2,4,6-tri-O-acetyl-3-deoxy-α-D-ribo-hexapyranoside (245 mg, 63%, 0.68 mmol) as a white solid. $^1$H NMR$^{[5]}$ (400 MHz, 298 K, DMSO-d$_6$): δ=7.11 (d, J=8.7 Hz, 1H), 4.81 (d, J=3.2 Hz, 1H), 4.79-4.76 (m, 1H), 4.73 (d, J=9.3 Hz, 2H), 4.15 (d, J=3.3 Hz, 2H), 4.10 (dd, J=9.0, 3.4 Hz, 1H), 3.30 (s, 3H), 2.00 (s, 3H), 1.97 (s, 3H), 1.89 (s, 3H), 1.88 (s, 3H).

Example 14

Synthesis of Methyl-3-acetamido-α-D-ribo-hexapyranoside

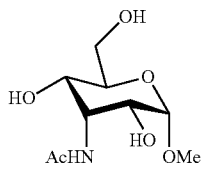

Methyl-3-acetamido-2,4,6-tri-O-acetyl-3-deoxy-α-D-ribo-hexapyranoside (Example 13; 141 mg, 0.39 mmol, 1.0 eq) was dissolved in dry methanol (1.4 mL). To this mixture, sodium methanolate (1 M, 0.1 mL) was added and the reaction mixture was stirred overnight at rt upon which the reaction had finished as indicated by TLC (pentane/EtOAc 1:1). The reaction was quenched with acidic ion exchange resin (Amberlite® 120 H$^+$-form) and stirred for an additional 10 min. After passing over a short silica gel column, the solvent was removed in vacuo to give methyl-3-amido-α-D-ribo-hexapyranoside (90 mg, 99%, 0.38 mmol) as a sticky slightly red solid. $^1$H NMR (400 MHz, 298 K, DMSO-d$_6$): δ=6.71 (d, J=8.9 Hz, 1H, NH), 4.52 (d, J=3.0 Hz, 1H, 1-H), 4.38-4.30 (m, 1H, 3-H), 3.63 (dd, J=11.4, J=1.6 Hz, 1H, 6-H), 3.56 (dd, J=5.2, 2.7 Hz, 1H, 2-H), 3.46 (m, 1H, 6'-H), 3.43 (m, 2H, 4-H, 5-H), 3.32 (s, 3H, OCH$_3$), 1.88 (s, 3H, CH$_3$). $^{13}$C NMR (101 MHz, 298 K, DMSO-d$_6$): δ=170.9 (NHCOCH$_3$), 99.6 (CH, C-1), 68.8 (CH, C-4), 66.3 (CH, C-2), 66.0 (CH, 5-C), 60.7 (CH$_2$, C-6), 54.8 (OCH$_3$), 52.8 (CH, C-3), 23.6 (NHCOCH$_3$). gCOSY (400 MHz, 298 K, DMSO-d$_6$): δ ($^1$H)/δ ($^1$H)=6.71/4.34 (NH/3-H), 4.52/3.56 (1-H/2-H), 4.38-4.30/6.71, 3.56, 3.43 (3-H/NH, 2-H, 4-H), 3.63/3.46, 3.43 (6-H/6'-H, 5-H), 3.56/4.52, 4.34 (2-H/1-H, 3-H), 3.46/3.63, 3.43 (6'-H/6-H, 5-H), 3.43/4.34, 3.43 (4-H/3-H, 5-H), 3.43/3.63, 3.46 (5-H/6-H, 6'-H). gHSQC (400 MHz, 298 K, DMSO-d$_6$): δ ($^1$H)/δ ($^{13}$C)=4.52/99.63 (1-H/C-1), 4.38-4.30/52.75 (3-H, C-3), 3.63/60.73 (6-H/C-6), 3.56/66.34 (2-H/C-2), 3.46/60.73 (6'-H/C-6), 3.43/68.83 (4-H/C-4), 3.43/66.00 (5-H/C-5), 3.32/23.58 (OCH$_3$/OCH$_3$), 1.88/54.81 (CH$_3$/CH$_3$). NOESY (400 MHz, 298 K, DMSO-d$_6$): δ ($^1$H)/δ ($^1$H)=3.43/3.63, 3.56 (4-H/6-H, 2-H), 3.43/6.71, 1.88 (5-H/NH, CH$_3$). HRMS (ESI) calculated for $C_9H_{17}NO_6H$ ([M+H]$^+$): 236.1129. found: 236.1127, $C_9H_{17}NO_6Na$ ([M+Na]$^+$): 258.0948. found: 258.0947.

Example 15

Synthesis of Methyl-3-amino-β-D-ribo-hexapyranoside

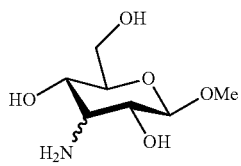

Methyl-3-O-methyloxime-β-D-ribo-hexapyranoside (Example 11B; 299 mg, 1.14 mmol, 1.0 eq) in acetic acid (5 mL) was hydrogenated over platinum(IV) oxide (26 mg, 0.14 mmol, 10 mol %) under hydrogen pressure (5 bar). The mixture was passed over a short celite column and was concentrated in vacuo, to give methyl-3-amino-α-D-ribo-hexapyranoside (267 mg, 1.14 mmol, 99%) as a sticky slightly yellow solid. The product was directly used in a subsequent per-acetylation reaction (Example 16) to separate diastereomers. $^1$H NMR[5] (400 MHz, 298 K, DMSO-$d_6$): δ=4.46 (d, J=7.6 Hz, 1H), 3.66-3.61 (m, 1H), 3.60-3.52 (m, 2H), 3.45 (dd, J=11.6, 5.0 Hz, 1H), 3.40 (d, J=3.3 Hz, 1H), 3.37 (s, 3H), 3.33 (dd, J=7.3, 4.2 Hz, 1H).

Example 16

Synthesis of Methyl-3-acetamido-2,4,6-tri-O-acetyl-3-deoxy-β-D-ribo-hexapyranoside

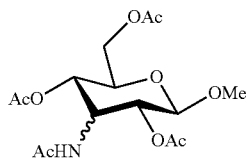

Methyl-3-amino-β-D-ribo-hexapyranoside (Example 15; 272 mg, 1.41 mmol, 1.0 eq) was dissolved in dry pyridine (2.8 mL) and acetic anhydride (1 mL, 11 mmol, 8 eq). The reaction mixture was stirred overnight and subsequently co-evaporated with toluene (1 mL) in vacuo, to give methyl-3-acetamido-2,4,6-tri-O-acetyl-3-deoxy-β-D-ribo-hexapyranoside as a white solid. The crude product was purified and the two diastereomers were separated by automatic silica gel column chromatography (GRACE) with a solvent gradient of pentane/EtOAc. 15 mg (3%) of pure C3-NHAc$_{aq}$ and 49 mg (10%) of C3-NHAc$_{ax}$ could be isolated along with 254 mg of mixed fractions (318 mg, 63%, 0.88 mmol). C3-NHAc$_{ax}$: $^1$H NMR[5] (400 MHz, 298 K, DMSO-$d_6$): δ=7.93 (d, J=9.6 Hz, 1H, NH), 4.80 (d, J=8.2 Hz, 1H, 1-H), 4.76 (dd, J=9.4, 4.6 Hz, 1H, 3-H), 4.70 (dd, J=9.1, 4.2 Hz, 1H, 4-H), 4.55 (dd, J=7.9, 4.6 Hz, 1H, 2-H), 4.20-4.10 (m, 3H, 5-H, 6-H, 6'-H), 3.39 (s, 3H, OCH$_3$), 2.03 (s, 3H, CH$_3$), 1.96 (s, 3H, CH$_3$), 1.93 (s, 3H, CH$_3$), 1.90 (s, 3H, CH$_3$). $^{13}$C NMR (101 MHz, 298 K, DMSO-$d_6$): δ=170.4 (COCH$_3$), 170.1 (COCH$_3$), 169.2 (COCH$_3$), 169.1 (COCH$_3$), 98.2 (CH, C-1), 69.7 (CH, C-5), 69.1 (CH, C-2), 66.3 (CH, C-4), 62.5 (CH$_2$, C-6), 55.9 (OCH$_3$), 46.0 (CH, C-3), 22.5 (NHCOCH$_3$), 20.6 (COCH$_3$), 20.5 (COCH$_3$), 20.5 (COCH$_3$). gCOSY (400 MHz, 298 K, DMSO-$d_6$): δ ($^1$H)/δ ($^1$H)=7.93/4.76 (NH/3-H), 4.80/4.55 (1-H/2-H), 4.76/7.93, 4.70, 4.55 (3-H/NH, 4-H, 2-H), 4.70/4.76, 4.16 (4-H/3-H, 5-H), 4.55/4.80, 4.76 (2-H/1-H, 3-H), 4.16/4.70, 4.16 (5-H/4-H, 6-H, 6'-H), 4.16/4.16 (6-H, 6'-H/5-H). gHSQC (400 MHz, 298 K, DMSO-$d_6$): δ ($^1$H)/δ ($^{13}$C)=4.80/98.20 (1-H, C-1), 4.76/46.01 (3-H/C-3), 4.70/66.34 (4-H/C-4), 4.55/69.12 (2-H/C-2), 4.16/69.71, 62.48 (5-H, 6-H, 6'-H/C-5, C-6) HRMS (ESI) calculated for C$_{15}$H$_{23}$NO$_9$H ([M+H]$^+$): 326.1446. found: 326.1443, C$_{15}$H$_{23}$NO$_9$Na ([M+Na]$^+$): 384.1265. found: 384.1261.

C3-NHAc$_{eq}$: $^1$H NMR (400 MHz, 298 K, DMSO-$d_6$): δ=7.94 (d, J=9.3 Hz, 1H, NH), 4.80 (dd, J=10.0 Hz, 10.0 Hz, 1H, 4-H), 4.70 (dd, J=10.5 Hz, 8.3 Hz, 1H, 2-H), 4.59 (d, J=7.8 Hz, 1H, 1-H), 4.19 (ddd, J=10.6 Hz, 10.0 Hz, 9.3 Hz, 1H, 3-H), 4.13 (m, 1H), 3.99 (m, 1H), 3.88 (ddd, J=10.0, 9.4, 3.1 Hz, 1H, 5-H), 3.36 (s, 3H, OCH$_3$), 2.01 (s, 3H, CH$_3$), 1.96 (s, 6H, CH$_3$), 1.71 (s, 3H, CH$_3$). $^{13}$C NMR (101 MHz, 298 K, DMSO-$d_6$): δ=170.1 (NHCOCH$_3$), 169.4 (2 COCH$_3$), 169.0 (COCH$_3$), 101.2 (CH, C-1), 71.8 (CH, C-5), 71.2 (CH, C-2), 68.6 (CH, C-4), 62.1 (CH$_2$, C-6), 56.2 (OCH$_3$), 52.0 (CH, C-3), 22.6 (NHCOCH$_3$), 20.6 (COCH$_3$), 20.5 (COCH$_3$), 20.4 (COCH$_3$). gCOSY (400 MHz, 298 K, DMSO-$d_6$): δ ($^1$H)/δ ($^1$H)=7.94/4.19 (NH/3-H), 4.80/4.19, 3.88 (4-H/3-H, 5-H), 4.70/4.59, 4.19 (2-H/1-H, 3-H), 4.59/4.70 (1-H, 2-H), 4.19/7.94, 4.80, 4.70 (3-H/NH, 4-H, 2-H), 4.13/3.99, 3.88 (CH$_2$/5-H, CH$_2$), 3.99/4.13, 3.88 (CH$_2$/CH$_2$, 5-H), 3.88/4.80, 4.13, 3.99 (5-H/4-H, CH$_2$, CH$_2$). gHSQC (400 MHz, 298 K, DMSO-$d_6$): δ ($^1$H)/δ ($^{13}$C)=4.80/68.59 (4-H/C-4), 4.70/71.19 (2-H, C-2), 4.59/101.25 (1-H, C-1), 4.19/51.99 (3-H/C-3), 4.13/62.08 (CH$_2$/C-6), 3.99/62.08 (CH$_2$/C-6), 3.88/71.83 (5-H/C-5) HRMS (ESI) calculated C$_{15}$H$_{23}$NO$_9$H ([M+H]$^+$): 326.1446. found: 326.1442, C$_{15}$H$_{23}$NO$_9$Na ([M+Na]$^+$): 384.1265. found: 384.1261.

Example 17

Oxidation of Neomycin B

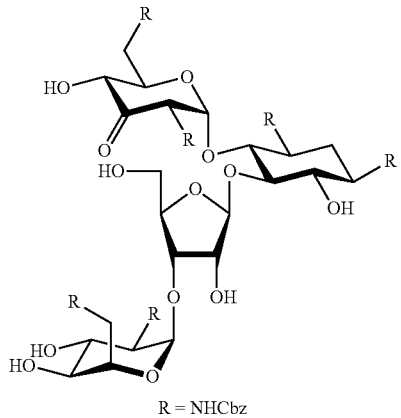

R = NHCbz

Carboxybenzyl (Cbz)-protected Neomycin B (190 mg, 134 μmol, 1.0 eq) and 2,6 dichlorobenzoquinone (71.1 mg, 402 μmol, 3.0 eq) were dissolved in 446 μL DMSO. [(2,9-dimethyl-1,10-phenanthroline)-Pd(μ-OAc)]2(OTf)2 (1.5 mg, 1.5 μmol 1.1 mol %) was added and the mixture was stirred over night. Water (5 mL) was added and the mixture was freeze-dried over night. Pure oxidized Cbz-protected Neomycin B (41 mg, 22%) was isolated after purification by column chromatography (eluent: gradient of DCM/MeOH 0-10%) along with mixed fractions. HRMS (ESI) calculated for C$_{71}$H$_{81}$N$_6$O$_{25}$ ([M+H]$^+$): 1417.5246. found: 1417.5122, C$_{71}$H$_{80}$N$_6$O$_{25}$Na ([M+Na]$^+$): 1439.5065. found: 1439.4911.

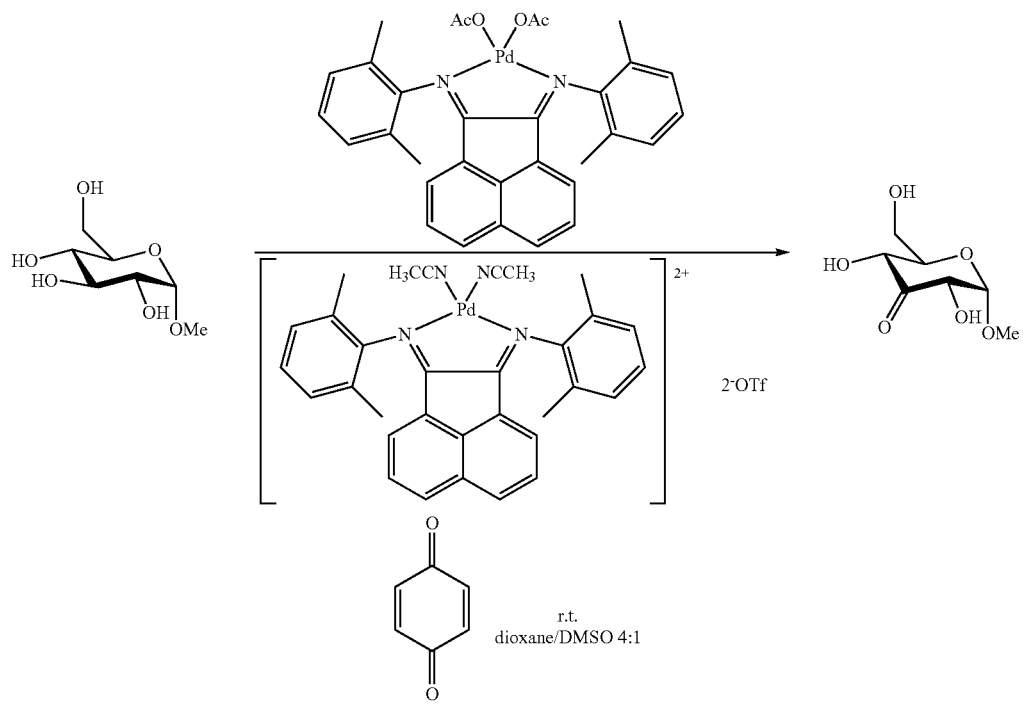

Example 18

Oxidation Using BIAN-Complexes

Methyl-α-D-glucopyranoside (30 mg, 0.15 mmol, 1.0 eq) and benzoquinone (50 mg, 0.46 mmol, 3.0 eq) were dissolved in a dioxane/DMSO mixture (4:1, 0.5 mL, 0.3 M). (Bis[N-(2,6-dimethylphenyl)imino]acenaphthene)-Pd-(OAc)2 (1.2 mg, 1.9 gmol, 1.25 mol %) and [(bis[N-(2,6-dimethylphenyl)imino]acenaphthene)-Pd-(CH3CN)2](OTf)2 (1.2 mg, 1.9 gmol, 1.25 mol %) were added. After the reaction was stirred over night at 60° C., NMR-spectroscopy showed conversion of 9% to the methyl-α-D-ribohexapyranosid-3-ulose (oxidation on C3) as single product.

Example 19

Oxidation of methyl-2-desoxy-α-glucopyranoside

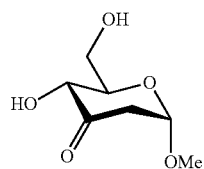

Methyl-2-desoxy-α-glucopyranoside (150 mg, 0.84 mmol, 1.0 eq) and 2,6-dichloro-1,4-benzoquinone (447 mg, 2.53 mmol, 3.0 eq) were dissolved in 2.5 mL dioxane/DMSO mixture (4:1, 0.3 M) and [(2,9-dimethyl-1,10-phenanthroline)-Pd(μ-OAc)]$_2$(OTf)$_2$ (22 mg, 2.5 mol %) was added. The mixture was stirred at rt for 30 min. The reaction was quenched by adding water (12 mL) and the resulting precipitate was filtered. The filter was washed with 3×2.25 mL of water and the combined water layers were passed over a charcoal column (12 g of charcoal). The charcoal column was washed with 4 column volumes of water and subsequently the product was eluted with water/acetonitrile 1:1 (2.5 column volumes). Methyl-2-deoxy-α-D-erythro-hexopyranosid-3-ulose (89 mg, 0.50 mmol, 60%) was obtained pure, after freeze drying, as greenish oil. $^1$H NMR (400 MHz, CD$_3$OD): δ 5.14 (d, J=4.3 Hz, 1H), 4.18 (dd, J=9.9, 1.1 Hz, 1H), 3.88 (dd, J=12.0, 2.3 Hz, 1H), 3.81 (dd, J=12.0, 4.7 Hz, 1H), 3.69 (ddd, J=9.9, 4.7, 2.3 Hz, 1H), 3.34 (s, 3H), 2.88 (ddd, J=14.1, 4.5, 1.1 Hz, 1H), 2.50 (dd, J=14.1, 1.1 Hz, 1H). $^{13}$C NMR (101 MHz, CD$_3$OD): δ 207.39 (C$_{quart.}$), 101.34 (CH), 76.53 (CH), 74.27 (CH), 62.79 (CH$_2$), 55.18 (CH$_3$), 46.80 (CH$_2$). HRMS (APCI) calculated for C$_7$H$_{13}$O$_5$ ([M+H]$^+$): 177.076. found: 177.075.

Example 20

Synthesis of phenyl-α-D-ribo-hexapyranoside-3-ulose

Phenyl-α-D-glucopyranoside (108 mg, 0.42 mmol, 1.0 eq) was dissolved in a dioxane/DMSO mixture (4:1, 1.3 mL, 0.32 M) and dichlorobenzoquinone (223 mg, 1.26 mmol, 3.0 eq) and [(2,9-dimethyl-1,10-phenanthroline)-Pd(μ-OAc)]$_2$(OTf)$_2$ (11 mg, 2.5 mol %) were added. The reaction was stirred for 30 min and was quenched by addition of 8 mL water. The mixture was filtered and the precipitates were washed with water (3×2 mL). The water layer was concentrated using a Genevac (T<40° C.), which gave 230 mg of crude product. The crude product was purified by column chromatography (21 g silica gel (SG2), eluent: DCM/MeOH 20/1, DCM was saturated with water), which gave 89 mg (contains about 13% DMSO according to $^1$H-NMR, 0.30 mmol, 73%) of pure phenyl-α-D-ribo-hexapyranoside-3-ulose. $^1$H NMR (400 MHz, CD$_3$OD): δ=7.29 (t, J=7.9 Hz, 2H), 7.13 (d, J=8.0 Hz, 2H), 7.03 (t, J=7.4 Hz, 1H), 5.83 (d, J=4.2 Hz, 1H), 4.58 (dd, J=4.2, 1.1 Hz, 1H), 4.38 (dd, J=9.0, 1.1 Hz, 1H), 3.85-3.74 (m, 3H). $^{13}$C NMR (101 MHz, CD$_3$OD): δ=206.9 (C$_{quart.}$), 158.2 (C$_{quart.}$), 130.7 (CH), 124.0 (CH), 118.2 (CH), 101.9 (CH), 77.7 (CH), 76.0 (CH), 73.3 (CH), 62.3 (CH$_2$). HRMS (ESI) calculated for C$_{12}$H$_{14}$O$_6$Na ([M+Na]$^+$): 277.068. found: 277.068.

Example 21

Synthesis of thiophenyl-β-D-ribo-hexopyranoside-3-ulose

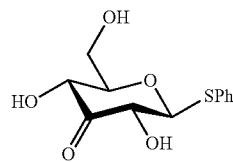

Phenylthio-β-glucopyranoside (229 mg, 0.84 mmol, 1.0 eq) and 2,6-dichloro-1,4-benzoquinone (446 mg, 2.53 mmol, 3.0 eq) were dissolved in 2.8 mL dioxane/DMSO mixture (4:1, 0.3 M) and [(2,9-dimethyl-1,10-phenanthroline)-Pd(μ-OAc)]$_2$(OTf)$_2$ was added portions wise over time (6.5 mol %, 57.2 mg 54.6 gmol in total, 4×1 mol % every 2 h then 2×1.0 mol % every 1 h and 1×0.5 mol % after 1 h). The mixture was stirred at rt for additional 1 h (12 h in total), no more starting material was observed by NMR-spectroscopy. The reaction was quenched by adding water (17 mL) and the resulting precipitate was filtered. The filter was washed with 3×2 mL of water and the combined water layers were passed over a charcoal column chromatography (10 g charcoal). The charcoal column was washed with 6 column volumes of water and subsequently with acetonitrile/water mixtures (25%, 50%, 75%, 100% acetonitrile, 200 ml each, 50% acetonitrile eluted the product) to elute the product. The fractions containing the product were freeze dried to give 107 mg (0.39 mmol, 47%) of pure product as white fluffy solid. $^1$H NMR (400 MHz, CD$_3$OD): δ 7.64-7.49 (m, 2H), 7.37-7.20 (m, 3H), 4.68 (d, J=10.0, 1H), 4.24 (dd, J=10.1, 1.4 Hz, 1H), 4.06 (dd, J=10.0, 1.4 Hz, 1H), 3.93 (dd, J=12.3, 2.0 Hz, 1H), 3.79 (dd, J=12.3, 4.9 Hz, 1H), 3.43 (ddd, J=10.1, 4.9, 2.0 Hz, 1H). $^{13}$C NMR (101 MHz, CD$_3$OD): δ=207.4, 134.0, 133.9, 130.1, 129.1, 91.0, 84.0, 76.1, 73.9, 62.8. HRMS (ESI) calculated for C$_{12}$H$_{14}$O$_5$SNa ([M+Na]$^+$): 293.045. found: 293.045.

Example 22

Oxidation of Methylallose

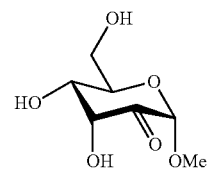

Methyl-allose (74 mg, 0.38 mmol, 1 eq) and 2,6-Dichlorobenzoquinone (202 mg, 1.14 mmol, 3 eq) were dissolved in 1.3 mL Acetonitril/water (10:1) mixture.). [(2,9-dimethyl-1,10-phenanthroline)-Pd(μ-OAc)]$_2$(OTf)$_2$ (10 mg, 9.5 μmol, 2.5 mol %) was added and the mixture was stirred at r.t. for 6 h. The reaction mixture was diluted with 1 mL water and was washed with 10 mL toluene. The water layer was washed with 5 mL ether. The water layer was filtered and concentrated to give a 3.6/1 mixture of oxidation on C2/C3 according to NMR, thus demonstrating the regioselectivity.

Example 23

Oxidation of myo-inositol

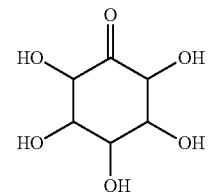

Myo-inositol (50 mg, 0.28 mmol, 1 eq) and 2,6-dichlorobenzoquinone (147 mg, 0.83 mmol, 3 eq) were dissolved in DMSO (0.9 mL). [(2,9-dimethyl-1,10-phenanthroline)-Pd(μ-OAc)]$_2$(OTf)$_2$ (7 mg, 7 gmol, 2.5 mol %) was added and the mixture was stirred at r.t. for 4.5 h. Reaction mixture was diluted with 1 mL water and was washed with 10 mL toluene and with 5 mL ether. The water layer was filtered and concentrated to give a 3:1 mixture of two oxidation products according to NMR.

REFERENCES

[1] For NMR-spectrum in D$_2$O see: G. de Wit, C. de Hann, A. P. G. Kieboom, H. van Bekkum, Carbohydr. Res. 1980, 86, 33-41.
[2] For NMR-spectrum in D$_2$O see: S. Freimund, A. Huwig, F. Giffhorn, S. Köpper, Chem. Eur. J. 1998, 4, 2442-2455.
[3] For NMR-spectrum in D$_2$O see: J. S. Brimacombe, A. Husain, Carbohydr. Res. 1968, 6, 491-493.
[4] For NMR-spectrum in D$_2$O see: C. H. Wong, Y. Ichikawa, T. Krach, C. Gautheron-Le Narvor, D. P. Dumas, G. C. Look, J. Am. Chem. Soc. 1991, 113, 8137-8145.
[5] For NMR-spectrum in D$_2$O or CDCl$_3$ see: H. H. Baer, Y. Gan, Carbohydr. Res. 1991, 210, 233-245.

The invention claimed is:
1. A process for the regioselective oxidation of a single secondary hydroxy function of a carbohydrate substrate comprising two or more secondary hydroxy functions, wherein the carbohydrate substrate is a neamine-based aminoglycoside antibiotic selected from the group consisting of neomycin, neamin, amikacin, paromomycin, ribostamycin, kanamycin, framycetin, isepamicin, and derivatives thereof, and wherein the single secondary hydroxyl function is the C3 hydroxyl of ring I of the neamine-backbone, comprising contacting the carbohydrate substrate in a solvent in the presence of a transition metal catalyst complex with an oxidizing agent to yield a mono-oxidized carbohydrate, and wherein the catalyst complex comprises at least one transition metal atom selected from palladium, ruthenium, copper, manganese and iron and one or more ligands comprising at least one nitrogen atom.

2. A process according to claim 1, wherein the transition metal catalyst complex comprises palladium.

3. A process according to claim 2, wherein the transition metal catalyst complex comprises at least one palladium atom and one or more ligands comprising at least one nitrogen atom.

4. A process according to claim 3, wherein the transition metal catalyst complex is a palladium phenanthroline or a palladium bis(aryl)acenapthenequinonediimine (BIAN) complex in which the phenanthroline or the BIAN ligand is optionally substituted.

5. A process according to claim 1, wherein the transition metal catalyst complex is used in a molar ratio of 0.01-10 mol % with respect to the carbohydrate substrate.

6. A process according to claim 1, wherein the oxidizing agent is selected from the group consisting of a quinone, oxygen, air, peroxide and hydroperoxide.

7. A process according to claim 1, wherein the process is performed at a temperature between 0-100° C.

8. A process according to claim 1, wherein the oxidation reaction is performed in solvent containing water, DMSO, DMF, THF, dioxane, acetonitril, HMPA, NMP, or any mixture thereof.

9. Process according to claim 8, wherein the reaction is performed in a mixture of acetonitrile/water in a ratio of 4:1 to 20:1 (v/v), in DMSO, in a mixture of dioxane/water in a ratio of 4:1 to 20:1 (v/v), or dioxane/DMSO in a ratio of 4:1 to 20:1 (v/v).

10. Process according to claim 1, wherein the carbohydrate substrate does not carry any protecting groups on the secondary hydroxyl groups.

11. Process according to claim 1, wherein the mono-oxidized carbohydrate is subjected to a further derivatization reaction.

12. Process according to claim 11, wherein said further derivatization reaction comprises reduction, reductive amination, acetalisation, diazotation, hydrocyanation, imination, oximation, hydrazination, de-oxygenation, alkylation, or any combination thereof.

* * * * *

UNITED STATES PATENT AND TRADEMARK OFFICE
CERTIFICATE OF CORRECTION

PATENT NO. : 9,751,906 B2
APPLICATION NO. : 14/409604
DATED : September 5, 2017
INVENTOR(S) : Minnaard et al.

Page 1 of 2

It is certified that error appears in the above-identified patent and that said Letters Patent is hereby corrected as shown below:

On the Title Page

In item (30), in "Foreign Application Priority Data", in Column 1, Line 1, delete "12172787" and insert --12172787.9-- therefor On page 2, in Column 1, under "Other Publications", Line 4, delete "checmistry" and insert --chemistry-- therefor In the Claims In Column 23, Line 14, in Claim 2, delete "A" and insert --The-- therefor In Column 23, Line 16, in Claim 3, delete "A" and insert --The-- therefor In Column 23, Line 20, in Claim 4, delete "A" and insert --The-- therefor In Column 23, Line 25, in Claim 5, delete "A" and insert --The-- therefor In Column 24, Line 1, in Claim 6, delete "A" and insert --The-- therefor In Column 24, Line 4, in Claim 7, delete "A" and insert --The-- therefor In Column 24, Line 5, in Claim 7, delete "0-100° C." and insert --0-100 °C.-- therefor In Column 24, Line 6, in Claim 8, delete "A" and insert --The-- therefor In Column 24, Line 10, in Claim 9, delete "Process" and insert --The process-- therefor In Column 24, Line 15, in Claim 10, delete "Process" and insert --The process-- therefor Signed and Sealed this
Eighteenth Day of December, 2018

Andrei Iancu
*Director of the United States Patent and Trademark Office*

In Column 24, Line 19, in Claim 11, delete "Process" and insert --The process-- therefor In Column 24, Line 22, in Claim 12, delete "Process" and insert --The process-- therefor